United States Patent [19]

Alburger

[11] 3,948,092

[45] Apr. 6, 1976

[54] METHOD OF RECOVERING AND RE-CYCLING WATER-WASHABLE INSPECTION PENETRANTS

[76] Inventor: James R. Alburger, 5007 Hillard Ave., La Canada, Calif. 91011

[22] Filed: Jan. 13, 1975

[21] Appl. No.: 540,549

Related U.S. Application Data

[63] Continuation-in-part of Ser. No. 513,105, Oct. 8, 1974.

[52] U.S. Cl. .................................................. 73/104
[51] Int. Cl.² ........................................... G01N 21/16
[58] Field of Search ....................................... 73/104

[56] References Cited
UNITED STATES PATENTS

| | | | |
|---|---|---|---|
| 3,528,284 | 9/1970 | Skoglund et al. | 73/104 |
| 3,558,882 | 1/1971 | Mlot-Fijalkowski | 73/104 X |
| 3,764,265 | 10/1973 | Mlot-Fijalkowski | 73/104 X |

*Primary Examiner*—Richard C. Queisser
*Assistant Examiner*—John P. Beauchamp

[57] ABSTRACT

In the water-washable inspection penetrant process, a method and means for recovery of used penetrant in which penetrant-coated test parts are spray-washed in a pre-wash stripper step with water saturated with dissolved penetrant liquid. The saturated-water spray removes excess penetrant by the scrubbing action of spray droplets, but it cannot dissolve and deplete penetrant from crack entrapments. The thus-removed excess penetrant may be separated from the pre-wash water by flotation, and may be recovered for re-use. Following the pre-wash stripper-recovery step, the normal process of washing, drying, and inspection is resumed.

1 Claim, No Drawings

METHOD OF RECOVERING AND RE-CYCLING WATER-WASHABLE INSPECTION PENETRANTS

This application is a continuation-in-part of my copending application Ser. No. 513,105, filed Oct. 8, 1974, for AN OPEN-LOOP WATER-WASHABLE INSPECTION PENETRANT PROCESS.

RELATED PATENT APPLICATION

Appln. Ser. No. 431,236, filed Jan. 7, 1974, for WATER-WASHABLE INSPECTION PENETRANT EMPLOYING MINERAL SOLVENT AND A FATTY ACID SOLUBILITY PROMOTER.

Appln. Ser. No. 482,465, filed June 24, 1974, now U.S. Patent No. 3,896,664 for ENHANCED STABILITY WATER-WASHABLE PENETRANT COMPOSITION AND PROCESS, C.I.P. of Ser. No. 327,306, filed Jan. 29, 1973, Same Title.

Appln. Ser. No. 513,084, filed Oct. 8, 1974, for WATER-WASHABLE INSPECTION PENETRANT EMPLOYING TRIGLYCERIDES AND POLYCLYCERIDES OF FATTY ACIDS.

Appln. Ser. No. 513,104, filed Oct. 8, 1974, for AN OPEN-LOOP WATER-WASHABLE INSPECTION PENETRANT PROCESS.

Appln. Ser. No. 540,418, filed Jan. 13, 1975, for AN INHIBITED PREWASH STRIPPER COMPOSITION FOR WATER-WASHABLE INSPECTION PENETRANTS.

Appln. Ser. No. 532,830, filed Dec. 16, 1974, for METHOD AND MEANS OF ACCELERATING REMOVAL OF BACKGROUND ENTRAPMENTS IN THE INSPECTION PENETRANT PROCESS.

The present invention relates to the water-washable inspection penetrant process. More particularly, the invention relates to an improvement step in the process which provides for recovery and re-cycling of used penetrant, and which also provides certain benefits in the flaw detection performance features of the penetrant process.

The water-washable inspection penetrant process is used extensively for the nondestructive testing and inspection of critical aircraft parts, such as jet-engine turbine blades, for the presence of potential failure flaws in the nature of cracks, pinholes, forging laps, inter-granular corrosion defects, and other flaws which are open to the surface. The process, as normally used, includes several steps, as follows:

1. Application of the penetrant to test parts.
2. Wash-removal of surface penetrant.
3. Continuation of washing to deplete background entrapments.
4. Drying the parts.
5. Development of indications.
6. Inspection for the presence of defect indications.

Most water-washable penetrants which are currently in use throughout industry are the self-emulsifiable type, consisting of an oil vehicle containing a dissolved indicator dye and a combination of detergents and solvent couplers which act to form oil-in-water emulsions upon contact with water. The indicator dye may be visible-color, fluorescent, or both, in accordance with known practices.

In the conventional water-washable inspection penetrant process, a water-soluble or self-emulsifiable penetrant is applied to a test surface by dipping, brushing, spraying, or by other convenient means. After a brief dwell time, during which the penetrant liquid is allowed to penetrate into any cracks which are present, the test surface is washed with water, preferably by a spray of water. This spray-wash procedure is usually carried out as a single washing operation, but in reality the washing takes place in two distinct stages. First, the excess surface layer of penetrant is flushed away, and second, depletion of entrapments in cracks or surface porosities takes place upon continued washing.

The test parts are then dried and are allowed to stand so that entrapments of penetrant may exude from cracks by "self-development,", or alternatively a dry, wet, nonaqueous, or plastic-film developer may be used in accordance with known practices. Finally, the test parts are inspected for indications of crack entrapments, under white light or black light, depending on the nature of the indicator dye which is used.

In accordance with present day usage, the surface penetrant which is removed from test parts becomes mixed with the wash water and is discarded into the nearest sewage or water disposal system. In some cases, efforts are made to extract the penetrant from the wash water so as to minimize pollution in waste water effluents, but this is quite difficult in the case of readily soluble or easily emulsified penetrants.

Another feature of the conventional water-washable penetrant process is that the first stage of washing may require varying amounts of time, depending on the viscosity of the penetrant, the extent to which penetrant-coated surfaces have been drained, the orientation of such surfaces, and the presence of concavities, blind holes, etc. Thus, for a given total time of wash-water contact with a test part, the actual time during which depletion of crack and background porosity entrapments can take place (after surface penetrant removal) may vary considerably at different areas on the test part. Thus, the conventional water-washable process often exhibits severe variations in flaw detection performance for different parts or different areas of parts.

I have discovered that it is possible to modify the water-washable inspection penetrant process in such a way that most of the penetrant can be readily recovered for re-use. In addition, I have discovered that it is possible to improve the uniformity of flaw detection performance on test parts, regardless of their configuration of orientation of surfaces during processing.

The principal object of the invention, therefore, is to provide an improved water-washable inspection penetrant process which permits the recovery of used penetrant.

Another object of the invention is to provide an improved water-washable inspection penetrant process which produces greater uniformity in flaw detection performance.

These and other objects of the invention will in part be obvious, and will in part become apparent from the following specification.

In my copending Appln. Ser. No. 513,105, of which the present Appln. is a continuation-in-part, I have disclosed and claimed an "Open-Loop Process" in which parts to be tested are coated with a low-solubility penetrant. Then the parts are washed with water to strip off excess surface penetrant. The low-solubility character of the penetrant which is used permits the bulk of the stripped-off penetrant to be recovered by flotation-separation, and only a small quantity of dissolved penetrant escapes from the system in the overflow of wash water.

In accordance with this present invention, I have found it possible to further restrict the amount of penetrant which is carried out in the wash water effluent. In fact, I have found it possible to carry out the operation of wash-removal of surface penetrant from test parts without allowing any of the thus-removed penetrant to escape into a wash-water disposal system or sewer.

I have discovered that the introduction of an inhibited pre-wash stripper step into the water-washable penetrant process may act to remove excess surface penetrant for recovery and re-use. At the same time, this inhibited pre-wash step also acts to prepare test surfaces in such a way that a finish-wash operation depletes background entrapments and crack entrapments in a uniform manner over the entire test surface. This step of pre-wash stripping is a closed-loop system in itself, and is not open to sewage disposal, as will be hereinafter described.

The inhibited pre-wash stripper composition used in the process of the invention has been disclosed and claimed in my copending Appln. Ser. No. 540,418, filed Jan. 13, 1975, for AN INHIBITED PRE-WASH STRIPPER COMPOSITION FOR WATER-WASHABLE INSPECTION PENETRANTS. This pre-wash stripper composition consists of water which is saturated with dissolved penetrant. Since the water is completely saturated with penetrant, it is inhibited in its solvent action so that it cannot dissolve any additional penetrant. The saturated water solution is capable of removing surface penetrant from parts when applied by spray, but once this surface penetrant is removed, entrapments in cracks and surface porosities are not dissolved, even though the inhibited spray-wash is applied for a prolonged period of time.

The process of the present invention will function only with certain kinds of low-solubility water-washable penetrants. While some self-emulsifiable penetrants which contain less than a few percent of detergent constituents may be used, the preferred types of water-washable penetrants are the so-called "slow-solubility penetrants" which contain no detergent ingredients, and which are soluable in water only to concentrations in the range of about 0.001% up to about 3%. Several categories of slow-solubility penetrants are disclosed and claimed in my copending Applns. Ser. Nos. 431,236, 482,465, and 513,084. I have designated penetrants of these kinds as "slow-solubility penetrants" for the reason that their low-solubility characteristic causes them to dissolve slowly from crack entrapments in test parts. However, for the main purpose of this invention, the important feature of the slow-solubility penetrants is that they are capable of forming saturated solutions in water, and the thus-produced saturated solutions may be used as inhibited pre-wash stripper compositions in the process of the invention.

It will be understood, therefore, that the recovery process of the invention depends on the use of low-solubility penetrants, or penetrants which are not easily and extensively emulsifiable. Useful penetrants must be of a nature such that saturated solutions or mixtures of the penetrants may form in water. The recovery process involves a modification of the conventional water-washable penetrant method, in which I introduce a step of pre-wash stripping following the step of penetrant application, and prior to the step of depletion-washing of background entrapments. The sequence of process steps thus becomes the following:

1. Apply penetrant to test parts.
2. Apply a pre-wash stripper to remove surface penetrant.
3. Finish-wash to deplete background entrapments.
4. Dry the test parts.
5. Develop indications by self-development or by use of a particulate-type developer.
6. Inspect the parts under black light or white light, as applicable.

The above listing of process steps includes those steps which are essential for the method of use, recovery, and re-use of a slow-solubility water-washable penetrant. Certain additional steps may be introduced, if desired, as for example the step or steps of interim drying, as is disclosed and claimed in my copending Appln. Ser. No. 532,830, filed Dec. 16, 1974, for METHOD AND MEANS OF ACCELERATING REMOVAL OF BACKGROUND ENTRAPMENTS IN THE INSPECTION PENETRANT PROCESS.

For the implementation of the foregoing process, the preferred arrangement of apparatus is as follows. The inhibited pre-wash stripper solution may be contained in a reservoir tank which is large enough to hold a volume of saturated water solution of the penetrant along with a floating layer of penetrant liquid. When parts are to be processed, penetrant is first drawn from the floating layer and is applied to the test parts, or the parts may be dipped in the floating layer. The saturated pre-wash water is pumped from the bottom of this reservoir tank up to a spray nozzle or an arrangement of spray nozzles directed against the penetrant-coated test parts. Excess penetrant which is stripped off of the test parts is flushed down and returned to the wash-water reservoir, where it floats to the surface and combines with the layer of penetrant in the reservoir tank.

Accordingly, the inhibited pre-wash portion of the processing equipment is a self-contained re-circulating system. In actual practice, it is possible to carry out the pre-wash operation in a tank which is separate from other processing tanks or other apparatus used in the process. However, it will be understood that it is possible to carry out all of the steps of the process in a single tank, a trough, or even in a large room, merely by bringing appropriate spray nozzles or air-jet driers into play.

For example, large aircraft wing spars may be processed in a long trough, or large engine shrouds may be suspended by a chain-hoist in a large room. In either case, the test object may be sprayed sequentially with penetrant, pre-wash stripper, and finish-wash water, and dried by means of a compressed air gun. Liquids which collect on the bottom of the trough or on the floor of the processing room are returned to their appropriate reservoirs by means of suitable pumps and piping.

The inhibited pre-wash stripper step of the invention serves to remove and recover excess surface penetrant from test parts. This recovered penetrant represents the bulk of the penetrant which is used, and only a minute quantity of penetrant remains on the test surface in porosities and actual cracks. Of course, if no porosities or cracks exist, then all of the penetrant is recovered, except for a negligable amount which might be lost by splashing or carry-over of the pre-wash liquid.

The amount of penetrant which is retained on test parts after treatment with the pre-wash stripper is quite small, and the portion of such residues which are dissolved in the finish-wash is smaller still. Measurements of penetrant carry-over in the conventional water-washable process (without pre-wash stripping) showed a penetrant usage of about 1.25 gallons of penetrant in processing 1000 square feet of highly porous jet engine turbine blades. However, when the inhibited pre-wash stripping step of the invention is introduced into the process, the carry-over of penetrant into the finish-wash stage of the process was only about 0.2 gram. Accordingly, the efficiency of recovery of penetrant was considerably greater than 99.9%.

In practical usage of the process of the invention, some splashing and carry-over will usually take place above and beyond the above-indicated amounts. However, with reasonable care in the process operation, it would be expected that 1000 square feet of test parts can be processed through the pre-wash stripper of the invention and into a finish-wash water volume of about 500 gallons, while maintaining the contamination level in the finish-wash water below 5 parts per million. Hence, it is seen that the contamination of the finish-wash water by dissolved penetrant may be made negligably small, even less than 5 parts per million, depending on the flow rate of the finish-wash water and the manner in which the finish-wash water is circulated and replenished.

It will be understood that the finish-wash water may consist of fresh tap water, or it may be re-circulated from a reservoir tank. If this finish-wash water is supplied and re-circulated from a reservoir tank, it is necessary to allow an overflow and replenishment of the tank at a rate sufficient to maintain the contamination of the effluent water below an acceptable level.

Although the inhibited stripper step of the invention may be carried out at any desired temperature of the saturated wash water, a preferred temperature range for this process material is from about 100°F. to about 130°F. At such elevated temperatures, the viscosity of the penetrant on test parts is reduced, and the penetrant is more readily stripped off by spray-scrubber action. However, I make no restrictions on the operating temperatures, duration of washing, or other operational details of the process, since these are features which may be matters of preference or they may be varied in accordance with the character of parts being processed and the flaw detection results which are desired.

Although the invention has been described with reference to particular embodiments thereof, it will be understood that various changes may be made therein without departing from the spirit of the invention or the scope of the appended claims.

I claim:

1. In a water-washable inspection penetrant process for the detection of surface defects and discontinuities in test parts in which the following steps are carried out in sequence:
   a. Apply a water-washable dyed liquid penetrant to said test parts,
   b. Finish-wash the penetrant-treated test parts with water to deplete background entrapments of penetrant,
   c. Dry the said test parts,
   d. Develop indications of surface flaws on said test parts, and
   e. Inspect said test parts for indications of flaw entrapments, the improvement which provides for the recovery of excess penetrant, in which the following step is introduced immediately following step (a) of penetrant application and prior to step (b) of finish-washing with water:
   Spray-wash said test parts with an inhibited pre-wash stripper solution,
   whereby excess surface penetrant is stripped off of said test parts and is recovered by flotation separation, said pre-wash stripper solution consisting of water which is saturated with dissolved penetrant, and said water-washable penetrant being a slow-solubility type dyed liquid having a solubility in water within the range of about 0.001% to 3%.

* * * * *